(12) United States Patent
Baskin et al.

(10) Patent No.: US 11,198,898 B2
(45) Date of Patent: Dec. 14, 2021

(54) CHEMICAL TOOLS FOR IMAGING PHOSPHOLIPASE D ACTIVITY

(71) Applicant: CORNELL UNIVERSITY, Ithaca, NY (US)

(72) Inventors: Jeremy Baskin, Ithaca, NY (US); Timothy Bumpus, Ithaca, NY (US); Dongjun Liang, Ithaca, NY (US)

(73) Assignee: CORNELL UNIVERSITY, Ithaca, NY (US)

( * ) Notice: Subject to any disclaimer, the term of this patent is extended or adjusted under 35 U.S.C. 154(b) by 0 days.

(21) Appl. No.: 16/131,798

(22) Filed: Sep. 14, 2018

(65) Prior Publication Data

US 2019/0085373 A1 Mar. 21, 2019

Related U.S. Application Data

(60) Provisional application No. 62/559,056, filed on Sep. 15, 2017.

(51) Int. Cl.
| | | |
|---|---|---|
| *C12Q 1/42* | (2006.01) | |
| *C07C 233/60* | (2006.01) | |
| *C07C 33/05* | (2006.01) | |
| *C07C 43/196* | (2006.01) | |
| *C07C 235/08* | (2006.01) | |
| *C07D 321/12* | (2006.01) | |
| *C07D 313/18* | (2006.01) | |

(52) U.S. Cl.
CPC ............... *C12Q 1/42* (2013.01); *C07C 33/05* (2013.01); *C07C 43/196* (2013.01); *C07C 233/60* (2013.01); *C07C 235/08* (2013.01); *C07D 313/18* (2013.01); *C07D 321/12* (2013.01); *C07C 2601/02* (2017.05); *C07C 2601/18* (2017.05); *G01N 2333/916* (2013.01)

(58) Field of Classification Search
CPC combination set(s) only.
See application file for complete search history.

(56) References Cited

U.S. PATENT DOCUMENTS

| 5,321,145 A | 6/1994 | Schafer | |
| 2005/0026235 A1* | 2/2005 | Graham | G01N 33/92 435/21 |

FOREIGN PATENT DOCUMENTS

WO   2016025480 A1   2/2016

OTHER PUBLICATIONS

Grammel, M. et al. Nat. Chem Biol. 2013 vol. 9, pp. 475-484.*
Knall A-C. et al., "Inverse electron demand Diels-Alder (iEDDA)-initiated conjugation: a (high) potential click chemistry scheme", Chem. Soc. Rev., (2013), 42, pp. 5131-5142 DOI: 10.1039/c3cs60049a.
Patterson D.M. et al., "Functionalized Cyclopropenes as Bioorthogonal Chemical Reporters", J. Am. Chern. Soc., (2012), 134, pp. 18638-18643 dx.doi.org/10.1021/ja3060436.
Li Z. et al., "Tetrazine-trans-cyclooctene ligation for the rapid construction of 18F labeled probes", Chem. Commun., (2010), 46, pp. 8043-8045 DOI: 10.1039/c0cc03078c.
Lambert W.D. et al., "Computationally guided discovery of a reactive, hydrophilic trans-5-oxocene dienophile for bioorthogonal labeling", Org. Biomol. Chem., (2017), 15, pp. 6640-6644 DOI: 10.1039/c7ob01707c.
Brown H.A. et al., "Biochemical Analysis of Phospholipase D", Methods Enzymol., (2007), 434, pp. 49-87 DOI: 10.1016/S0076-6879(07)34004-4.
Bumpus T.W. et al., "A Chemoenzymatic Strategy for Imaging Cellular Phosphatidic Acid Synthesis", Angew. Chem. Int. Ed. Engl., (2016), 55(42), pp. 13155-13158. PMCID: PMC5153663 DOI: 10.1002/anie.201607443.
McDermott M. et al., "Phospholipase D1,2", Biochem. Cell Biol., (2004), 82(1), pp. 225-253 doi: 10 1139/o03-079.
Su W. et al., "5-Fluoro-2-indolyl des-chlorohalopemide (FIPI), a Phospholipase D Pharmacological Inhibitor That Alters Cell Spreading and Inhibits Chemotaxis", Mol. Pharmacol., (2009), 75(3), pp. 437-446. PMCID: PMC2684902 doi:10.1124/mol.108.053298.
Alamudi S.H. et al., "Development of background-free tame fluorescent probes for intracellular live cell imaging", Nat. Commun., (2016), 7, pp. 1-9 DOI: 10.1038/ncomms11964.
Exton J.H., "Minireview: Regulation of phospholipase D", FEBS Letters, (2002), 531, pp. 58-61.
Colley W.C. et al., "Phospholipase D2, a distinct phospholipase D isoform with novel regulatory properties that provokes cytoskeletal reorganization", Current Biology, (1997), 7(3), pp. 191-201.
Nelson R.K. et al., "Physiological and pathophysiological roles for phospholipase D", J. Lipid Res., (2015), 56(12), pp. 2229-2237 DOI 10.1194/jlr.R059220.
Chen, Y.G., et al., "Phospholipase D Stimulates Release of Nascent Secretory Vesicles from the trans-Golgi Network", The Journal of Cell Biology, Aug. 11, 1997, pp. 495-504, vol. 138, No. 3.

* cited by examiner

*Primary Examiner* — Heidi Reese
(74) *Attorney, Agent, or Firm* — Scully, Scott, Murphy & Presser, P.C.

(57) ABSTRACT

A method for detecting phospholipase D (PLD) activity in a cell, comprising: (i) stimulating endogenous PLD in said cell for said PLD to catalyze a transphosphatidylation reaction between phosphatidylcholine or a derivative thereof and an exogenous functionalized alcohol to form a phosphatidyl alcohol, wherein the functionalized alcohol possesses a first functional group that can react with and form a bond to a functionalized detectable label having a second functional group reactive with the first functional group, and said phosphatidyl alcohol contains said first functional group in available form; (ii) reacting said phosphatidyl alcohol with said functionalized detectable label under conditions where said functionalized detectable label reacts, via its second functional group, with the first functional group to form a linkage between said detectable label and said phosphatidyl alcohol so as to form a labeled phosphatidyl alcohol containing said detectable label; and (iii) detecting said labeled phosphatidyl alcohol.

28 Claims, 9 Drawing Sheets

CHEMICAL TOOLS FOR IMAGING PHOSPHOLIPASE D ACTIVITY

CROSS REFERENCE TO RELATED APPLICATION

This application claims the benefit of priority from U.S. Provisional Application No. 62/559,056, filed on Sep. 15, 2017.

FIELD OF THE INVENTION

The present invention relates generally to the imaging of phospholipase D (PLD) activity, and more specifically, to imaging methods in which a product resulting from PLD activity is tagged with a detectable label.

BACKGROUND OF THE INVENTION

Signal transduction pathways allow cells to translate biochemical cues from the extracellular environment into changes in metabolism, gene expression, and behavior. Second messengers are key signaling intermediates in these pathways whose downstream effects depend greatly on cell type, physiological state, and, importantly, the intracellular location of their production. Because the spatial regulation of signaling is so critical for ensuring desired physiological outcomes, imaging-based tools have become indispensable for studying the dynamics of signaling events within live cells.

Phospholipase D enzymes impact intracellular signaling by synthesizing the pleiotropic lipid second messenger phosphatidic acid (PA). PLD-mediated synthesis of PA leads to diverse physiological changes, including modifications to membrane curvature, vesicle trafficking, and the actin cytoskeleton as well as activation of protein kinases. These changes ultimately cause modulations in cell growth, division, migration, and other behaviors. To achieve such a diverse set of physiological outcomes from a sole signaling agent, cells use multiple upstream signals to selectively activate different PLD isozymes at specific locations to control PA production spatiotemporally. Indeed, several enzyme isoforms responsible for PA biosynthesis—most notably members of the PLD, diacylglycerol kinase, and lysophosphatidic acid acyltransferase families—have been extensively characterized, and their subcellular localizations and enzymatic activities are all carefully controlled. Among these, the PLD family has been implicated as a major producer of PA upon cell stimulation under both physiological and pathological conditions. Given that PA initiates a diversity of signaling events and is produced on several organelle membranes by different biosynthetic enzymes, it is challenging to attribute biological functions to individual subcellular pools of PA with currently available tools. To dissect the multiple functions of PA, the ability to detect and resolve spatially distinct pools of PA produced by these different enzymatic pathways is critically needed.

Several strategies currently exist to image PLD signaling, each with its strengths and drawbacks. Fluorescent protein fusions have revealed dynamic localizations of PLD1 and PLD2, the two isozymes responsible for PA generation via hydrolysis of phosphatidylcholine (PC). It is now well appreciated, however, that the localization of total enzyme pools often does not correlate well with the subpopulations that are active. Conversely, there exist several genetically encoded probes to directly visualize PA, consisting of positively-charged, PA-binding peptides fused to fluorescent proteins. However, these probes generally cannot distinguish between different biosynthetic pools of PA originating from PLDs, diacylglycerol kinases, or lysophosphatidic acid acyltransferases. Furthermore, these probes can perturb signaling by masking the target lipid, and their binding often depends on additional ligands or membrane bilayer properties, leading to biased localizations. Thus, improved methods of PLD signal imaging without such impediments are needed and would represent a significant advance in the field.

SUMMARY OF THE INVENTION

The present disclosure is foremost directed to a novel method for detecting PLD activity in a cell. The method advantageously provides a number of benefits, including: i) visualizing where phospholipase D enzymes are actively synthesizing phosphatidic acid both at the individual cell level in a population of cells and at the subcellular organelle level within a cell; ii) real-time PLD activity imaging in live cells; iii) distinguishing PLD-derived PA from PA from other biosynthetic sources and quantifying such PA pools; and iv) synthesizing unnatural functionalized lipids with alkyne, azido, and other bio-orthogonally tagged head groups for biochemical analysis using PLD enzymes as catalysts.

The method for imaging PLD activity includes the following steps: (i) stimulating endogenous PLD in the cell while the cell is in contact with an exogenous functionalized alcohol containing at least one carbon atom in order for the PLD to catalyze a transphosphatidylation reaction between phosphatidylcholine or a derivative thereof and the exogenous functionalized alcohol to form a phosphatidyl alcohol, wherein the exogenous functionalized alcohol possesses a first functional group that can react with and form a bond to a functionalized detectable label having a second functional group reactive with the first functional group, and the phosphatidyl alcohol contains the first functional group in available form, as provided by the exogenous functionalized alcohol; (ii) reacting the phosphatidyl alcohol with the functionalized detectable label under conditions where the functionalized detectable label reacts, via its second functional group, with the first functional group on the phosphatidyl alcohol, to form a linkage between the detectable label and the phosphatidyl alcohol so as to form a labeled phosphatidyl alcohol containing the detectable label; and (iii) detecting the labeled phosphatidyl alcohol.

In particular embodiments, the phosphatidyl alcohol, as produced in step (i), has the following generic structure:

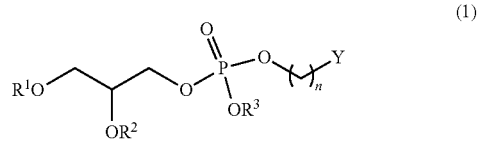

(1)

wherein: $R^1$ and $R^2$ are independently selected from acyl fatty acid groups —C(O)R, wherein R is independently selected from alkyl or alkenyl groups having at least 12 carbon atoms; $R^3$ is a H atom, hydrocarbon group having 1-3 carbon atoms, or a cationic species; n is an integer of 1-12; and Y is said first functional group. The functional group Y can be any group capable of reacting with a second functional group on the functionalized detectable label to form a covalent or bioconjugate linkage between the first and second functional groups. In particular embodiments, the group Y is an alkynyl, azido, cyclopropene, or trans-cyclooctene group.

In another aspect, the invention is directed to certain novel cyclopropene alcohols and trans-cyclooctene alcohols capable of undergoing transphosphatidylation reactions with phosphatidylcholine in the presence of PLD to form useful phosphatidyl alcohol intermediates that can be labeled via an IEDDA cycloaddition reaction as described above. Some examples of such alcohols include:

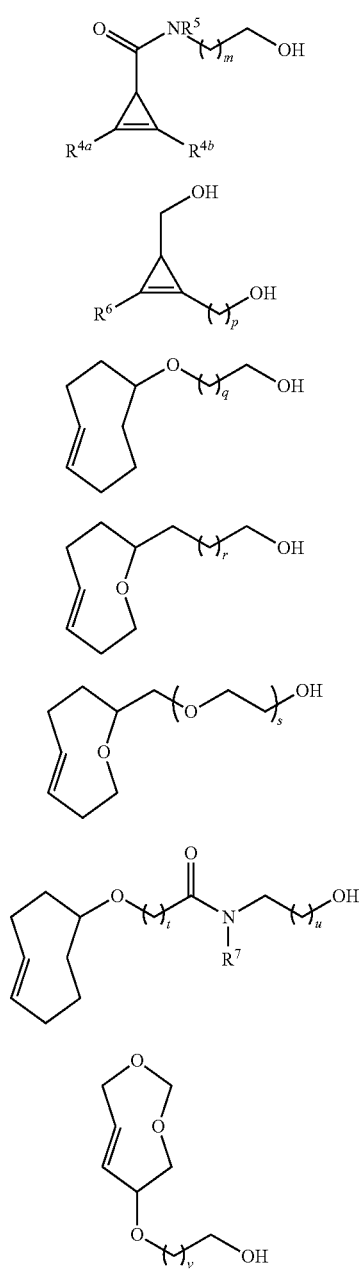

The above-described method is useful for imaging sites of cellular PA synthesis by PLD enzymes. PLD enzymes are known to hydrolyze phosphatidylcholine (PC) to generate PA and choline. The method described herein exploits the ability of PLD enzymes to also catalyze transphosphatidylation reactions with exogenously supplied primary alcohols (e.g., butanol) to generate unnatural phosphatidyl alcohols. FIG. 1 shows two schematics: (A) the natural hydrolysis of PC to PA and choline, and (B) the transphosphatidylation reaction with exogenously supplied primary alcohols. The transphosphatidylation reaction occurs with rapid kinetics, which allows simple primary alcohols to effectively compete inside living cells with water in the PLD active site. In some embodiments, the process can be used for measurement (quantification) of endogenous phospholipase D activity in cell lines, in primary disease samples (e.g., cancer, inflammation) from biopsies and surgical material.

While existing approaches enable accurate measurement of cellular PLD activity and have seen extensive use in probing the biological effects of PA synthesis, they generally require ex vivo analysis, and hence, do not provide spatial information on the sites of PA synthesis within the cell. Given that several PLD isoforms exist and are localized to different intracellular membrane compartments, the location of PA production is thought to be critical to the numerous physiological effects of this signaling lipid. In contrast, the present method uses transphosphatidylation but enables the phosphatidyl alcohol lipid to be subsequently tagged using linking (e.g., click) chemistry with a detectable tag, enabling detection in vitro by TLC. HPLC, LC-MS, and also by imaging techniques within live cells (in vivo), such as fluorescence-activated cell sorting and fluorescence microscopy.

Genetically encoded biosensors are commonly used for imaging cellular phospholipids. These probes typically contain a naturally occurring or engineered lipid-binding domain fused to a fluorescent protein. Although these sensors are widely used, they do have some drawbacks, such as binding to additional molecules than the desired lipid, sequestration of the target lipid (thus disrupting its function), and an inability to report on minor lipid pools because of competitive binding to major lipid pools. Several PA biosensors have been reported, with the most frequently used ones containing a 40-amino acid PA-binding domain from the yeast protein Spo20p. Studies were herein undertaken to compare the presently described labeling to an optimized version of a PA biosensor probe, and partial overlap of the fluorescence signals was observed, particularly at the plasma membrane. Complete colocalization was not observed, which highlights the differences between equilibrium binding of a biosensor to pools of PA on different membranes produced by several biosynthetic routes, with the presently described approach, which targets de novo synthesis exclusively by PLD enzymes but generates unnatural PA mimics. In short, the biosensors can exhibit biased localizations and report on all PA in the cell whereas the presently described method reports on PA synthesized by PLD enzymes exclusively and does not rely on weak electrostatic binding to lipid head groups.

BRIEF DESCRIPTION OF THE FIGURES

FIG. 2A is a schematic showing transphosphatidylation of a series of alkynols on phosphatidylcholine followed by copper-mediated binding of an azido-fluorophore (Az-488) via alkyne-azide cycloaddition. FIG. 2B shows HPLC-fluorescence traces for the resulting labeled phosphatidyl alcohols (as shown in FIG. 2A) derived from five alkynols (denoted as 1, 2, 3, 4, or 5 in panels 1-5, respectively).

DETAILED DESCRIPTION OF THE INVENTION

Figure 1:
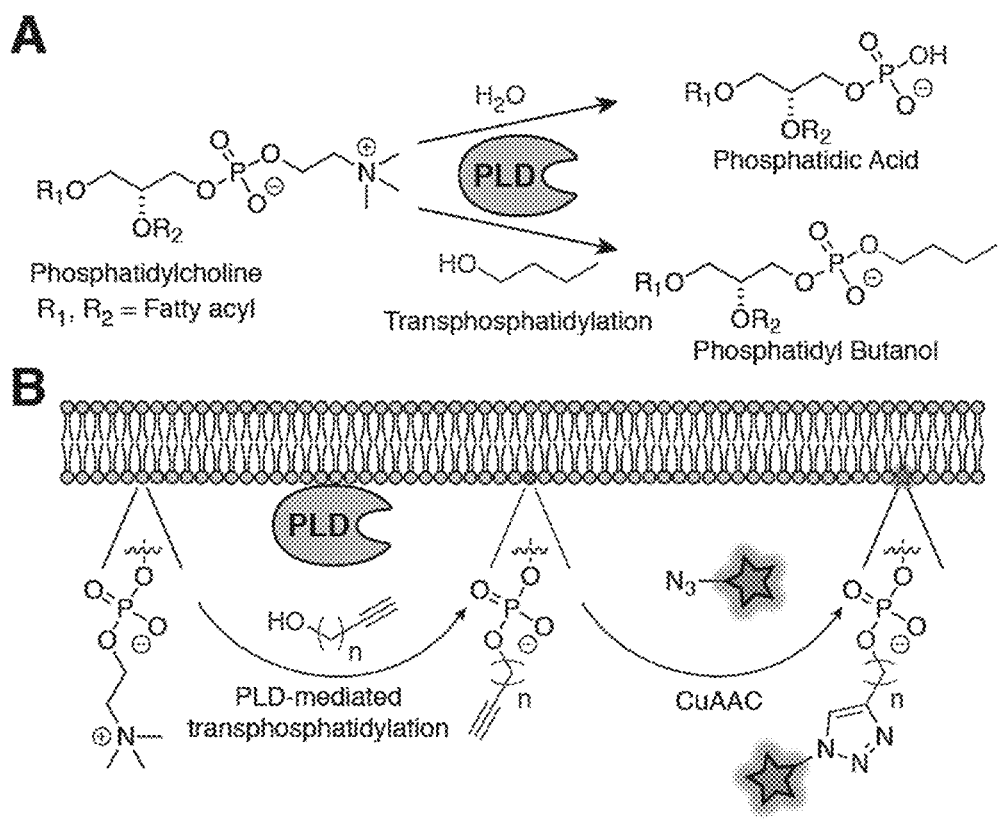
FIG. 1 shows the following two schematics: (A) the hydrolysis of PC to PA and choline, i.e., PLD physiologically catalyzes hydrolysis of phosphatidylcholine to form PA (top) and can also mediate transphosphatidylation reactions with short-chain primary alcohols (e.g., butanol) to form phosphatidyl alcohols (bottom), and (B) the transphosphatidylation reaction with exogenously supplied primary alcohols, and two-step approach to image PLD-mediated PA synthesis wherein cells are treated with alkynols, thus resulting in PLD-mediated formation of phosphatidyl alkynols, followed by CuAAC labeling with an azido fluorophore to enable visualization or quantification.

The present invention is foremost directed to a method for detecting PLD activity in a living cell. The term "living cell" includes cells living in vitro and in vivo, such as in a mammal, typically human. As further discussed below, the method uses the ability of PLD to effect a transphosphatidylation reaction between phosphatidylcholine or a derivative thereof and an exogenous functionalized alcohol (typically, a primary alcohol) to form a phosphatidyl alcohol containing a reactive functional group (as derived from the functionalized alcohol) for subsequent binding of a detectable label.

The transphosphatidylation reaction can be schematically depicted as follows:

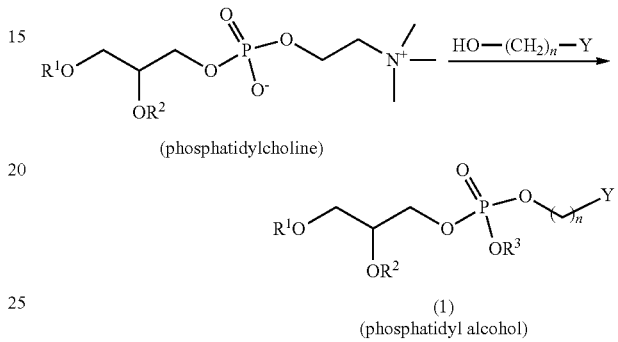

In the above schematic, $R^1$ and $R^2$ are independently selected from acyl fatty acid groups —C(O)R, wherein R is independently selected from alkyl or alkenyl groups having at least 12 carbon atoms; $R^3$ is a H atom, hydrocarbon group having 1-3 carbon atoms (e.g., methyl, ethyl, n-propyl, or isopropyl), or a cationic species (e.g., lithium, sodium, potassium, or ammonium); n is an integer of 1-12; and Y is a first functional group that can react with and form a bond to a functionalized detectable label having a second functional group reactive with the first functional group. The phrase "first functional group" may, in some embodiments, refer only to the functional group itself (e.g., —N$_3$ or —C≡CH). The phrase "first functional group" may, in other embodiments, also include any group containing the functional group (e.g., phenyl-azide or cyclooctyne).

The phosphatidylcholine (PC) may, in a first embodiment, be naturally produced (endogenous) PC, i.e., 1-oleoyl-2-palmitoyl-phosphatidylcholine (wherein $R^1$ is oleoyl and $R^2$ is palmitoyl). However, the method can also utilize a derivative of PC, which corresponds to $R^1$ and/or $R^2$ being acyl fatty acid groups —C(O)R other than in naturally occurring PC, wherein R is independently selected from alkyl or alkenyl groups having at least 12 carbon atoms. $R^1$ and $R^2$ can be independently selected from any of the saturated and unsaturated acyl fatty acid groups known in the art. Some examples of saturated acyl fatty acid groups include myristoyl, palmitoyl, and stearoyl. Some examples of unsaturated acyl fatty acid groups include oleoyl, palmitoleoyl, and linoleoyl. The derivative of PC may, in addition or alternatively, have one or more of the three methyl groups on the positively-charged choline replaced with other hydrocarbon groups, e.g., ethyl, propyl, or butyl groups. The derivative of PC is typically exogenously introduced into the cell.

The exogenous functionalized alcohol (i.e., "alcohol") contains at least or more than one, two, three, or four carbon atoms. Typically, the exogenous functionalized alcohol is a primary alcohol, such as an alcohol having the formula HO—(CH$_2$)$_n$—Y, wherein n is typically within the range of 1-12, e.g., 1, 2, 3, 4, 5, 6, 7, 8, 9, 10, 11, or 12, or a value within a range bounded by any two of the foregoing values. Aside from carbon atoms attributed to methylene groups subtended by n, the alcohol may include additional carbon atoms in the group Y. At least for this reason, the alcohol can have an overall carbon count of more than 12.

For purposes of the present invention, the exogenous functionalized alcohol possesses a first functional group (Y) that can react with and form a permanent bond to a functionalized detectable label having a second functional group reactive with the first functional group. The functional group Y can be any of a wide variety of crosslinking groups known to be reactive and form a bond (e.g., covalent or strong conjugation bond) with another reactive group. The functional group Y may be, for example, a carboxylic acid, carboxylic acid ester, amine, succinimide, azido, alkynyl, maleimide, aldehyde, halogen (e.g., chloro, bromo, or iodo), hydrazide, isocyanate, or isothiocyanate group. As well known, under suitable reaction conditions, carboxylic acid and carboxylic acid ester groups can react with amino or hydroxy groups to form amide or ester linkages, respectively; amine groups can react with carboxylic acid and carboxylic acid ester groups to form amide linkages; succinimide groups can react with amino groups to form amide linkages; azido groups can react with alkynyl groups via an azide-alkyne cycloaddition reaction to form a 1,2,3-triazole linkage, similarly, alkynyl groups can react with azido groups via an azide-alkyne cycloaddition reaction to form a 1,2,3-triazole linkage; maleimide groups can react with thiol groups to form a thioether linkage; and halogen atoms can react with amine groups to form a carbon-nitrogen linkage. In other embodiments, the functional group Y can be a cyclopropene or trans-cyclooctene functional group, which can react with a 1,2,4,5-tetrazine group via an inverse electron-demand Diels-Alder (IEDDA) cycloaddition reaction to form a dihydropyridazine or pyridazine linkage. In yet other embodiments, the functional group Y can be a bioconjugation linking group, such as biotin, which can conjugate with avidin (or streptavidin), or vice-versa.

In some embodiments, the group Y (e.g., alkynyl, azide, cyclopropene or trans-cyclooctene functional group) and hydroxy group on the alcohol are separated by the greatest number of carbon atoms in the alcohol. Some examples of such alcohols include 4-pentyn-1-ol, 5-hexyn-1-ol, 6-heptyn-1-ol, 7-octyn-1-ol, 5-azido-1-pentanol, 6-azido-1-hexanol, 7-azido-1-heptanol, and 8-azido-1-octanol.

In a first set of particular embodiments, the exogenous functionalized alcohol is an alkynol, and the alkynol reacts with the phosphatidylcholine or a derivative thereof to form the phosphatidyl alcohol, in which case the phosphatidyl alcohol contains an alkynyl functional group in available form, as provided by the alkynol. In particular embodiments, the alkynol is an acyclic alkynol. Some examples of acyclic alkynols include propargyl alcohol, 3-butyn-1-ol, 4-pentyn-1-ol, 5-hexyn-1-ol, 6-heptyn-1-ol, 7-octyn-1ol, 8-nonyn-1-ol, 9-decyn-1-ol, 10-undecyn-1-ol, and 1-dodecyn-1-ol. In other embodiments, the alkynol is a cyclic alkynol, such as a cyclooctynol.

In the case of an acyclic alkynol, the resulting phosphatidyl alcohol, as produced in step (i), can be represented by the following structure:

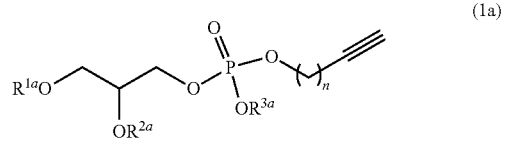

(1a)

In Formula (1a), $R^{1a}$ and $R^{2a}$ are independently selected from acyl fatty acid groups —C(O)R, wherein R is independently selected from alkyl or alkenyl groups having at least 12 carbon atoms, as described above; $R^{3a}$ is a H atom, hydrocarbon group having 1-3 carbon atoms, or a cationic species, as described above; and n is an integer of 1-12, as described above. In embodiments of the present invention, the alkyne-functionalized phosphatidyl alcohol in Formula (1a) can be reacted with an azide-functionalized detectable label under conditions where the alkyne group and azide group undergo an azide-alkyne cycloaddition reaction so as to form a labeled phosphatidyl alcohol that is detectable via the detectable label. In some embodiments, the azide-alkyne cycloaddition reaction is copper catalyzed. In other embodiments, the azide-alkyne cycloaddition reaction is a strain-promoted azide-alkyne cycloaddition (SPAAC) reaction, which typically does not employ a copper catalyst (i.e., is copper-free). The SPAAC reaction generally requires that the alkyne group is in the form of a cycloalkyne ring on the phosphatidyl alcohol.

In a second set of particular embodiments, the exogenous functionalized alcohol is an azido alcohol, and the azido alcohol reacts with the phosphatidylcholine or a derivative thereof to form the phosphatidyl alcohol, in which case the phosphatidyl alcohol contains an azido functional group in available form, as provided by the azido alcohol. Some examples of azido alcohols include 2-azidoethanol, 3-azido-1-propanol, 4-azido-1-butanol, 5-azido-1-pentanol, 6-azido-1-hexanol, 7-azido-1-heptanol, 8-azido-1-octanol, 9-azido-1-nonanol, 10-azido-1-decanol, 11-azido-1-undecanol, and 12-azido-1-dodecanol. The resulting phosphatidyl alcohol, as produced in step (i), can thus be represented by the following structure:

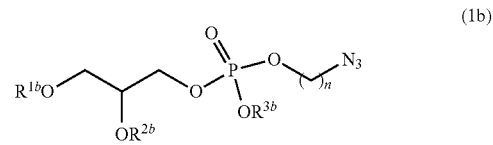

(1b)

In Formula (1b) above, $R^{1b}$ and $R^{2b}$ are independently selected from acyl fatty acid groups —C(O)R, wherein R is independently selected from alkyl or alkenyl groups having at least 12 carbon atoms, as described above; $R^{3b}$ is a H atom, hydrocarbon group having 1-3 carbon atoms, or a cationic species, as described above; and n is an integer of 1-12, as described above. In embodiments of the present invention, the azide-functionalized phosphatidyl alcohol in Formula (1b) can be reacted with an alkyne-functionalized detectable label under conditions where the azide group and alkyne group undergo an azide-alkyne cycloaddition reaction so as to form a labeled phosphatidyl alcohol that is detectable via the detectable label.

In a third set of particular embodiments, the exogenous functionalized alcohol is a cyclopropene alcohol or trans-cyclooctene alcohol, and the cyclopropene alcohol or trans-cyclooctene alcohol reacts with the phosphatidylcholine or a derivative thereof to form the phosphatidyl alcohol, in which case the phosphatidyl alcohol contains a cyclopropene or trans-cyclooctene functional group in available form, as provided by the cyclopropene alcohol or trans-cyclooctene alcohol. The resulting phosphatidyl alcohol, as produced in step (i), can thus be represented by the following structure:

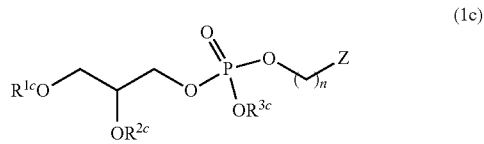

(1c)

In Formula (1c) above, $R^{1c}$ and $R^{2c}$ are independently selected from acyl fatty acid groups —C(O)R, wherein R is independently selected from alkyl or alkenyl groups having at least 12 carbon atoms, as described above; $R^{3c}$ is a H atom, hydrocarbon group having 1-3 carbon atoms, or a cationic species, as described above; n is an integer of 1-12, as described above; and Z is a cyclopropene or trans-cyclooctene functional group. In embodiments of the present invention, the cyclopropene- or trans-cyclooctene-functionalized phosphatidyl alcohol in Formula (1c) can be reacted with a tetrazine-functionalized detectable label under conditions where the cyclopropene or trans-cyclooctene group undergoes an inverse electron-demand Diels-Alder (IEDDA) cycloaddition reaction with the tetrazine so as to form a labeled phosphatidyl alcohol that is detectable via the detectable label. The IEDDA reaction is discussed in detail in, for example, A.-C. Knall et al., *Chem. Soc. Rev.,* 42, 5131-5142, 2013, the contents of which are herein incorporated by reference.

In some embodiments, the cyclopropene alcohol has any of the following structures:

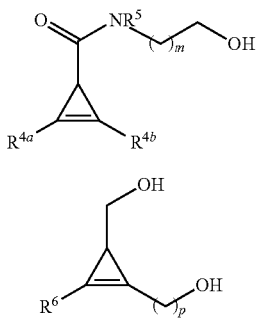

(2)

(3)

wherein $R^{4a}$, $R^{4b}$, $R^5$, and $R^6$ are independently selected from H atom and hydrocarbon groups containing 1-3 carbon atoms; and m is an integer of 1 to 12. Such compounds can be synthesized by any suitable means. In particular embodiments, compounds (2) and (3) are produced by cyclopropenation of the corresponding alkyne with ethyldiazoacetate and $Rh_2(OAc)_4$ followed by, for compounds (2), hydrolysis of the resultant methyl ester with KOH and amide formation with the appropriate aminoalcohol or, for compounds (3), reduction with DIBAL or $LiAlH_4$ followed by deprotection of a TBDPS group to reveal the second alcohol group, analogous to synthetic routes reported in Patterson et al., *J. Am. Chem. Soc.* 2012, 134, 18638-18643.

In some embodiments, the trans-cyclooctene alcohol has any of the following structures:

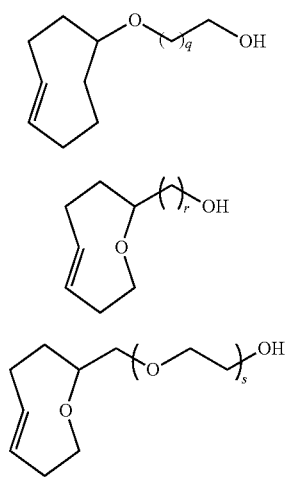

(4)

(5)

(6)

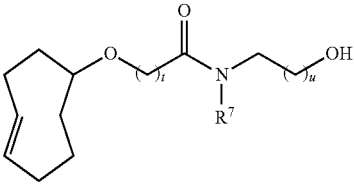

(7)

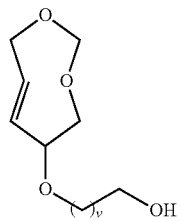

(8)

In the above structures (4)-(8), q and r are independently an integer of 1 to 12 (or within any range therein); s is an integer of 1 to 100 (or within any range therein, such as 1-50, 1-20, 2-100, 2-50, 2-20, 3-100, 3-50, or 3-20); $R^7$ is selected from H atom and hydrocarbon groups having 1-3 carbon atoms; t is 0 or 1; u is an integer of 1 to 12 (or within any range therein); v is an integer of 1 to 12 (or within any range therein); and w is an integer of 1 to 100 (or within any range therein). Such compounds can be synthesized by any suitable means. For example, compounds according to Formula (4) can be produced by reaction of cyclooct-4-en-1-ol with bromoacetic acid and sodium hydride, reduction with $LiAlH_4$, and photoisomerization with 254 nm UV light using methyl benzoate and capture of the product on $AgNO_3$-functionalized silica gel (q=1), analogously to the route reported by Li et al., *Chem. Commun.,* 2010, 46, 8043-8045, or reaction of cyclooct-4-en-1-ol with allyl bromide and sodium hydride followed by hydroboration with 9-BBN and subsequent oxidative workup with $H_2O_2$ and finally photoisomerization as above (q=2). Compounds according to formulas (5) and (6) can be synthesized by protection of the appropriate epoxyalcohol with TBDPSCl, epoxide opening with allyl magnesium chloride and $Li_2CuCl_4$, alcohol substitution with MOMCl followed by reaction with allyltrimethylsilane, Grubbs I-mediated cyclooctene formation, TBDPS deprotection with TBAF, and finally photoisomerization as above, analogous to the route reported by Lambert et al., *Org. Biomol. Chem.* 2017, 15, 6640-6644. Compounds according to formula (7) can be synthesized by reaction of cyclooct-4-en-1-ol with bromoacetic acid and sodium hydride, amide formation using the corresponding aminoalcohol in the presence of EDC and HOBt, and finally photoisomerization as above. Compounds according to formulas (8) can be synthesized by cyclopropenation of cis-4,7-dihydro-1,3-dioxepin with ethyl diazoacetate and $Rh_2(OAc)_4$, ester hydrolysis with LiOH, urea formation using a four-step sequence of ethyl chloroformate and triethylamine in acetone, sodium azide in water, reflux in toluene, and ammonia in THF, nitrosylation with $N_2O_4$ and sodium acetate in ethyl ether, and finally, stereospecific trans-alkene formation using sodium bicarbonate, trapping with the appropriate diol (e.g., ethylene glycol for v=1), analogous to Hilderbrand et al., WO2016025480 (A1), 2016.

As discussed above, after producing the above-described phosphatidyl alcohol containing a first functional group in step (i), the phosphatidyl alcohol is reacted in step (ii), via its first functional group, with a functionalized detectable label possessing a second functional group reactive with the first functional group. The end result is the formation of a linkage between the detectable label and the phosphatidyl alcohol so as to form a labeled phosphatidyl alcohol containing the detectable label. For example, the functionalized detectable label may be an azide-functionalized detectable label, which can be reacted, via its azide group, with a phosphatidyl alcohol functionalized with an alkyne group by azide-alkyne cycloaddition; or, for example, the functionalized detectable label may be an alkyne-functionalized detectable label, which can be reacted, via its alkyne group, with a phosphatidyl alcohol functionalized with an azide group by azide-alkyne cycloaddition; or, for example, the functionalized detectable label may be a tetrazine-functionalized detectable label, which can be reacted, via its tetrazine group, with a phosphatidyl alcohol functionalized with a cyclopropene or trans-cyclooctene group by an IEDDA cycloaddition reaction.

The detectable label can be any species known in the art that can be detected and used for imaging in a cell. The detectable label may be, for example, a fluorophore, radioisotope, or metal-containing nanoparticle. The fluorophore label can be detected and imaged by, for example, fluorescence-activated cell sorting and fluorescence microscopy, which may or may not be in combination with electrospray ionization-mass spectrometry (ESI-MS) detection. The radioisotope label can be detected and imaged by radionuclide (nuclear) detection, such as, for example, single-photon emission computed tomography (SPECT) or positron emission tomography (PET). Metal-containing nanoparticles may be detected using optical imaging or magnetic resonance imaging (MRI), the latter being particularly used in the case of paramagnetic nanoparticles.

In some embodiments, the detectable label is a fluorophore, typically an organic fluorophore. The fluorophore can be, for example, a charged (i.e., ionic) molecule (e.g., sulfonate or ammonium groups), uncharged (i.e., neutral) molecule, saturated molecule, unsaturated molecule, cyclic molecule, bicyclic molecule, tricyclic molecule, polycyclic molecule, acyclic molecule, aromatic molecule, and/or heterocyclic molecule (i.e., by being ring-substituted by one or more heteroatoms selected from, for example, nitrogen, oxygen and sulfur). The unsaturated fluorophores may contain one or more carbon-carbon and/or carbon-nitrogen double and/or triple bonds. In some embodiments, the fluorophore is a fused polycyclic aromatic hydrocarbon (PAH) containing at least two, three, four, five, or six rings (e.g., naphthalene, pyrene, anthracene, chrysene, triphenylene, tetracene, azulene, and phenanthrene) wherein the PAH can be optionally ring-substituted or derivatized by one, two, three or more heteroatoms or heteroatom-containing groups.

The fluorophore may also be a xanthene derivative, such as fluorescein, rhodamine, or eosin; cyanine, or its derivatives or subclasses, such as the streptocyanines, hemicyanines, closed chain cyanines, phycocyanins, allophycocyanins, indocarbocyanines, oxacarbocyanines, thiacarbocyanines, merocyanins, and phthalocyanines; naphthalene derivatives, such as the dansyl and prodan derivatives; coumarin and its derivatives; oxadiazole and its derivatives, such as the pyridyloxazoles, nitrobenzoxadiazoles, and benzoxadiazoles; pyrene and its derivatives; oxazine and its derivatives, such as Nile Red, Nile Blue, and cresyl violet; acridine derivatives, such as proflavin, acridine orange, and acridine yellow; arylmethine derivatives, such as auramine, crystal violet, and malachite green; and the tetrapyrrole derivatives, such as the porphyrins and bilirubins. Some examples of such dyes include the Cy® family of dyes (e.g., Cy2, Cy3, Cy3B, Cy3.5, Cy5, Cy5.5, and Cy7), the Alexa® family of dyes, the ATTO® family of dyes, and the Dy® family of dyes. The fluorophore may also be a dipyrromethene dye, such as boron-dipyrromethene (BODIPY). The fluorophore may alternatively be an inorganic type of fluorophore, such as a quantum dot nanoparticle. Some examples of quantum dot compositions include sulfides, selenides, and tellurides of gallium, indium, or cadmium.

In some embodiments, the detectable label is a detectable radioisotope. Some examples of radioisotopes include phosphorus-32, phosphorus-33, technetium-99m, thallium-201, technetium-97m, technetium-94m, technetium-94, iodine-123, iodine-124, iodine-131, fluorine-18, tin-121, gallium-67, gallium-68, rhenium-186, xenon-133, and rhenium-188. Such radioisotopes are particularly suited for detection and imaging in such diagnostic techniques as PET and SPECT.

In some embodiments, the detectable label is a metal-containing nanoparticle. For purposes of the invention, the metal in the metal-containing nanoparticle is typically in its zerovalent state, and typically a noble metal. The metal-containing nanoparticle may include or be completely composed of, for example, gold, silver, palladium, or platinum. Such nanoparticles are particularly suited for detection and imaging by microscopy or surface plasmon resonance (SPR) spectroscopy. The use of SPR in imaging of cellular processes using gold nanoparticles is described in, for example, X. Huang et al., *Journal of Advanced Research*, 1(1), 13-28, January 2010, the contents of which are herein incorporated by reference.

Examples of functionalized detectable labels include azide-functionalized rhodamine dyes, azide-functionalized cyanine dyes, alkyne-functionalized rhodamine dyes, alkyne-functionalized cyanine dyes, fluorescein isothiocyanate, BODIPY-cyclooctyne, azide-functionalized and alkyne-functionalized quantum dot nanoparticles, and N-hydroxysuccinimide (NHS) derivatized fluorescein, rhodamine, or cyanine dyes. Such functionalized detectable labels are either commercially available or can be synthesized by means well known in the art.

Examples have been set forth below for the purpose of illustration and to describe the best mode of the invention at the present time. However, the scope of this invention is not to be in any way limited by the examples set forth herein.

EXAMPLES

General Concept

The following experiments describe a process for imaging PLD-mediated PA synthesis within cells wherein butanol is replaced with an alkyne- or azide-functionalized alcohol (alkynol or azidoalcohol) that is used as a transphosphatidylation substrate by PLDs to permit subsequent detection by copper-catalyzed azide-alkyne cycloaddition (CuAAC) with an azido fluorophore or copper-free click chemistry/strain-promoted azide-alkyne cycloaddition (SPAAC). A general overview of the two-step process is provided schematically in FIG. 1, parts A and B. This two-step approach using a chemical reporter strategy permits both visualization and quantification of PLD-mediated PA synthesis within intact cells.

To image the dynamics of PLD-dependent PA synthesis, the process described herein capitalizes on the ability of PLD enzymes, which normally hydrolyze PC to generate PA, to accept small primary alcohols in a transphosphatidylation reaction to produce phosphatidyl alcohols. Transphosphatidylation with ethanol or 1-butanol has been widely used to assay PLD activity in vitro by thin-layer chromatography or mass spectrometry (Brown H A, et al., *Methods Enzynol.* 2007 Jan. 1:434:49-87). Because high concentrations of alcohols are typically used (0.1-1.5%, or approx. 10-300 mM), this method can block the PLD-mediated production of PA and can lead to undesired physiological effects. It was recently reported that PLDs can accept alkynols as substrates, with detection of PLD activity enabled at much lower alcohol concentrations due to subsequent probe tagging using the copper-catalyzed azide-alkyne cycloaddition (CuAAC) (Bumpus T W, et al., *Angew. Chem. Int. Ed. Engl.* 2016 Oct. 10:55(42):13155-8. PMCID: PMC5153663). While this approach could be used to image cellular PLD activity, due to the toxicity of copper, alkynols are not suitable PLD probes to follow the dynamics of PLD activity and signaling within live cells.

Herein is presented a chemical method to dynamically image pools of PA produced by PLD. The two-step strategy involves stimulation of endogenous PLD activity in the presence of an azidoalcohol to generate a phosphatidyl azidoalcohol, followed by tagging using copper-free click chemistry to append imaging or other detection probes. Significantly, the present approach does not perturb endogenous PA levels, and the cytocompatibility of copper-free click chemistry permits the imaging of dynamics of PLD activity, revealing unexpected localizations for its production of PA.

Use of Alkynyl Alcohols for Imaging in Fixed Cells Only

Figure 2A:
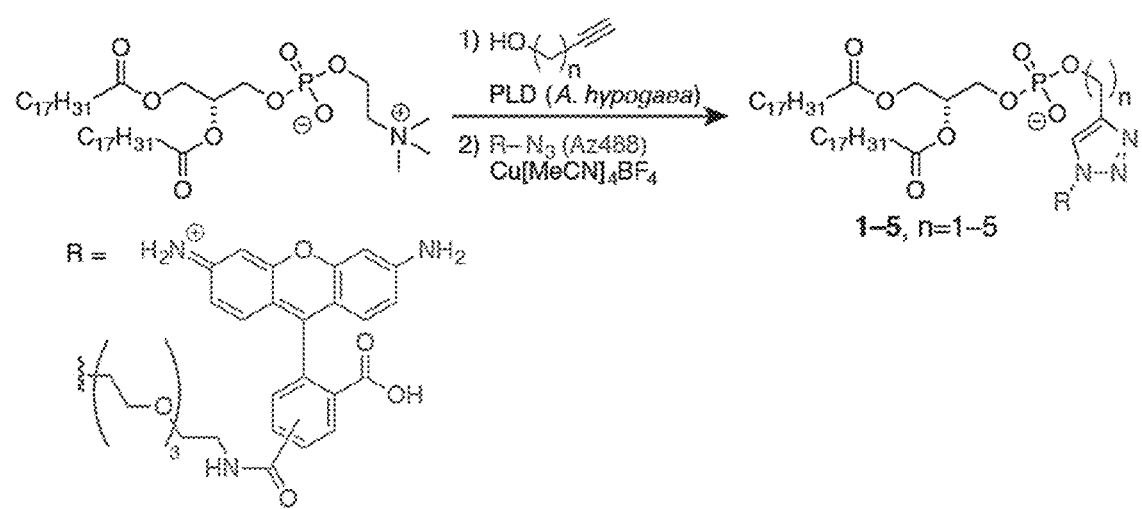
FIGS. 2A, 2B.

The first experiments assessed whether PLD would accept alkynols as substrates in vitro. A panel of five small alkynols (propynol, 3-butyn-1-ol, 4-pentyn-1-ol, 5-hexyn-1-ol, and 6-heptyn-1-ol) were evaluated by incubating each with 1,2-dioleoyl-sn-glycero-3-phosphocholine (DOPC) and a commercially available PLD. The reaction mixtures were then subjected to CuAAC with an azide-labeled rhodamine 110 derivative (Az488). HPLC separation coupled to fluorescence or electrospray ionization-mass spectrometry (ESI-MS) detection confirmed the identity of the expected fluorescent phosphatidyl alcohol products for all five alkynols. A general schematic of the process is provided in FIG. 2A.

Figure 2B:
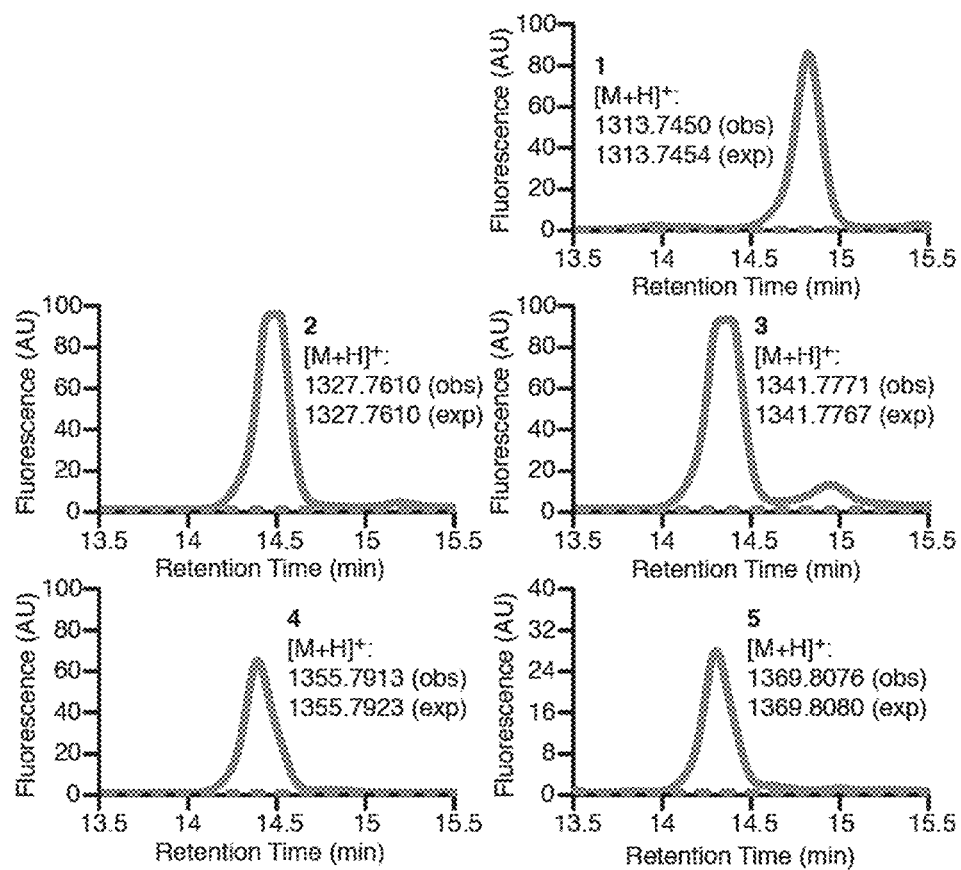

Further experiments evaluated whether mammalian PLDs would accept alkynols as substrates within live cells. HeLa cells were treated with each of the five alkynols for 20 minutes, stimulated acute PA biosynthesis pharmacologically using phorbol 12-myristate 13-acetate (PMA) (McDermott M, et al., Biochem. Cell Biol. 2004 February; 82(1):225-53), and then isolated total cellular lipid extracts. Following CuAAC labeling with Az488, the samples were analyzed by HPLC coupled to fluorescence detection. The HPLC-fluorescence results for the five alkynols (denoted as 1, 2, 3, 4, or 5 in panels 1-5, respectively) are shown in FIG. 2B. Comparison of these spectra to those from cells labeled in the presence of a well-characterized pan-PLD inhibitor, 5-fluoro-2-indolyl deschlorohalopemide (FIPI) (Su W, et al. *Mol. Pharmacol.* 2009 March; 75(3):437-46. PMCID: PMC2684902), demonstrated that fluorescent lipids were indeed produced as a result of PLD activity.

While all five alkynols were accepted as transphosphatidylation substrates in HeLa cells, they were processed by cellular PLDs with different efficiencies. It was found that, at the same concentration, the three longer chain alkynols (pentynol, hexynol, and heptynol) were incorporated to a greater extent into phosphatidyl alcohols compared to the shorter alkynols. The molecular identities of the fluorescently labeled phosphatidyl alcohols (PA analogs) were verified by analyzing labeled extracts from cells treated with each of the three longer-chain alkynols by HPLC followed by ESI-MS. These studies revealed the presence of several PA analogs differing in fatty acid chain lengths and degrees of unsaturation.

This robust labeling with pentynol, hexynol, and heptynol led to further experiments to investigate whether the dose of alkynol could be lowered. The initial concentration of 12.9 mM alkynol corresponded to the low end of the concentration range of 0.1-0.5 mol % that is typically used in the traditional TLC-based butanol transphosphatidylation assay. Such high concentrations of alcohol, however, have several negative consequences. First, they are sufficient to compete with water in the PLD active site and reduce the ability of PLDs to synthesize PA, thus impacting PA-dependent signaling. Second, recent studies with PLD knockout mice and selective inhibitors, such as FIPI, have revealed off-target effects for short-chain alcohols when used at these high concentrations. Thus, different concentrations of hexynol were screened, from which it was found that PA production could be detected in cells at concentrations as low as 100 µM.

To image sites of PLD-mediated PA synthesis, HeLa cells were treated with each of the three longer-chain alkynols and again stimulated PLD activity acutely with PMA, in the absence or presence of FIPI. Rather than proceeding with a whole-cell lipid extraction, cells were fixed with paraformaldehyde and subjected to CuAAC labeling with Az488. Confocal microscopy analysis revealed strong fluorescence labeling using all three alkynols, with minimal background labeling in two negative controls: (1) cells treated with alkynol and FIPI and (2) cells treated with no alkynol. It was found that hexynol provided the highest signal-to-background ratio, and thus, hexynol was used for all subsequent imaging experiments. As a further control to ensure that the protocol was principally labeling phospholipids (as opposed to cellular proteins), it was found that the labeling was sensitive to treatment with the detergent Triton X-100. To minimize the impact on cell metabolism and physiology, it was found that hexynol concentrations as low as 100 µM could permit detection of hexynol-dependent and FIPI-sensitive fluorescence. The observed labeling pattern was complex, likely the result of PA synthesis on membranes of multiple intracellular compartments. To determine the subcellular locations of the hexynol-based labeling, a series of colocalization studies were performed with markers of various organelle membranes. In these studies, HeLa cells were transfected with plasmids encoding fluorescent protein fusions to constituents of several organellar membranes and then the PA labeling protocol was performed using 1 mM hexynol and, where appropriate, either Az488 or an azide-containing tetramethylrhodamine derivative.

Imaging Results with Azidoalcohols

Figure 3:
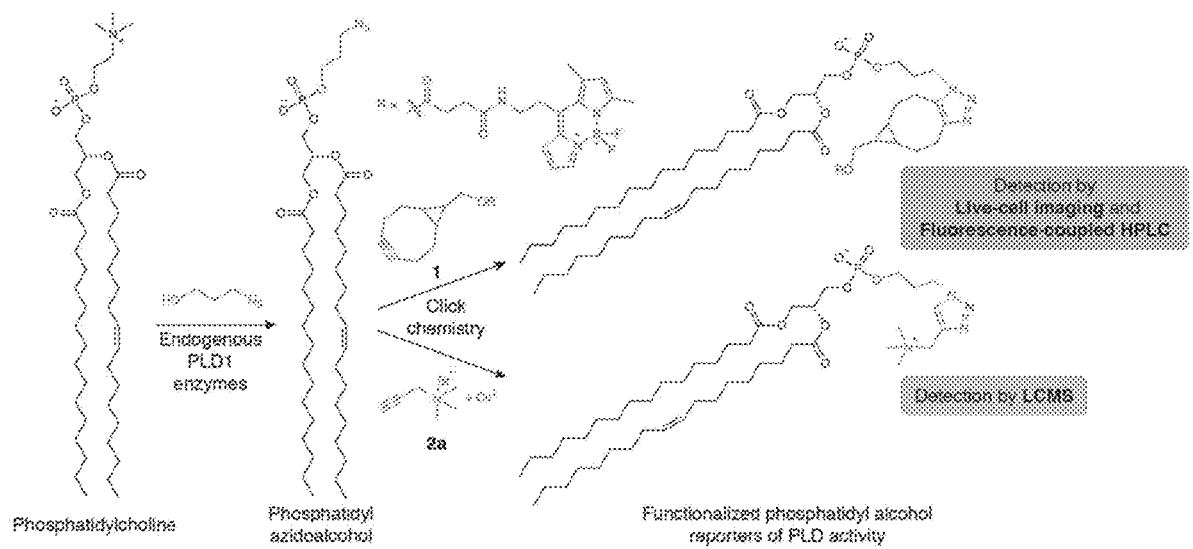
FIG. 3 is a general schematic of a process for monitoring PLD activity in cells using an azidoalcohol and a cycloalkynol containing a fluorophore (BODIPY) or a terminal alkyne containing a quaternary ammonium tag for mass spectrometry detection in an azide-alkyne cycloaddition (click chemistry) process.

An initial experiment began by treating HeLa cells with a panel of azidoalcohols: 2-azidoethanol (AzEt), 3-azido-1-propanol (AzProp), 4-azido-1-butanol (AzBut), and 5-azido-1-pentanol (AzPent). Endogenous PLD activity was stimulated using phorbol 12-myristate 13-acetate (PMA). Following lipid extraction and tagging by strain-promoted azide-alkyne cycloaddition (SPAAC) with BODIPY-cyclooctyne 1 (Alamudi S H, et al. *Nat. Commun. Nature Publishing Group;* 2016 Jun. 9; 7:1-9), HPLC analysis revealed the presence of fluorescent lipid species for all azidoalcohols tested. The above-described process for monitoring PLD activity using azidoalcohols and click chemistry is provided in FIG. 3.

Importantly, treatment of cells during the labeling procedure with the pan-PLD inhibitor 5-fluoro-2-indolyl deschlorohalopemide (FIPI) led to complete loss of the fluorescent lipid species, confirming that the fluorescently labeled lipids were derived exclusively from PLD activity. Isoform-selective PLD inhibitors were then used to assess the relative contributions of PLD1 and PLD2. Treatment with isoform-selective PLD1 (VU0359595) or PLD2 (VU0364739) inhibitors led to decreases in approximately 75% and 25%, respectively, of the signal. These data demonstrate that the disclosed method can report on both PLD1 and PLD2 activity and is consistent with the majority of PMA-stimulated PLD activity deriving from the PLD1 isozyme (Exton J H, *FEBS Letters,* 531(1):58-61, 2002). In terms of efficacy, AzProp, AzBut, and AzPent all performed roughly equivalently, while AzEt was a poorer PLD substrate.

Imaging with Azidoalcohols by SPAAC, in Live Cells

Having established that azidoalcohols such as AzProp could effectively serve as effective and non-perturbative reporters of endogenous PLD1 activity, experiments were conducted to image the dynamics of PLD1-dependent PA synthesis in live cells. Cells were incubated with various azidoalcohols and PLD activity was stimulated with PMA. Subsequently, cells were labeled for 10 minutes with compound (1), a cell-permeable, cyclooctyne-fluorophore conjugate that exhibits minimal non-specific binding to cellular membranes (see FIG. 3). Following a brief rinse-out, the cells were imaged by confocal microscopy. From this, strong fluorescence labeling of several intracellular compartments were observed. Control experiments using FIPI, VU0359595, and VU0364739 again confirmed that the bulk of the labeling under PMA stimulation can be ascribed to PLD1 activity. Among the azidoalcohols, the signal-to-background was highest for AzProp and AzEt, possibly because excess alcohol was more easily rinsed out of cells for these more hydrophilic alcohols. Among these two, AzProp was selected due to its higher level of labeling in imaging and HPLC experiments.

To determine the subcellular localization of the fluorescent phosphatidyl alcohols, colocalization experiments were performed with various organelle markers. The majority of the labeling colocalized strongly with markers of the Golgi apparatus and ER. While PLD-dependent PA production at the Golgi apparatus is well documented for many physiological processes occurring on Golgi membranes, the observation of such strong and striking fluorescent phosphatidyl alcohol labeling of the ER was highly unexpected.

The ER is the principal cellular site of de novo phospholipid biosynthesis, in which PA is a central intermediate. However, PA pools in the ER are generally thought to be produced from glycerol 3-phosphate via acyltransferase activities, although there have been proposed functions for PLD-generated PA in promoting vesicle trafficking from the ER to the Golgi via the Sar1 GTPase. The data suggest, however, that a substantial fraction of inducible PLD activity occurs at ER membranes, which is surprising given limited evidence for functions and localizations of PLDs at ER membranes.

Of additional significance, a small number of bright puncta containing fluorescent phosphatidyl alcohols in each cell were observed. These puncta exhibited partial colocalization with markers of both lysosomes (LAMP 1) and endosomes (Rab5), consistent with known roles for PLD-generated PA on these organelles, including in mTOR activation and macroautophagy. Interestingly, only a subset of these organelles contained the labeled phosphatidyl alcohols.

Without being bound by theory, it was surmised that if the fluorescent phosphatidyl alcohols are indeed faithful reporters of PLD activity, then performing the AzProp/SPAAC labeling in cells overexpressing a fluorescently tagged PLD1 construct should result in increased fluorescent phosphatidyl alcohol production on PLD1-positive structures. Based on this, an mCherry-tagged PLD1 was generated, and it was found that, as expected for an overexpressed, tagged PLD1, it localized predominantly to puncta corresponding to lysosomes and endosomes.

When mCherry-PLD1-expressing cells were incubated with AzProp, followed by PMA stimulation and SPAAC labeling with (1), an increase in fluorescent phosphatidyl alcohol signal was observed in bright puncta that indeed colocalized with mCherry-PLD1. Strikingly, while virtually every fluorescent phosphatidyl alcohol spot was positive for mCherry-PLD1, only a small subset of mCherry-PLD1-positive puncta were positive for fluorescent phosphatidyl alcohol. These results suggest an unappreciated spatial heterogeneity in PLD activation at the subcellular level, wherein even under strong stimulation with PMA, only a subset of PLD enzymes are activated.

Up to this point, the efforts focused on monitoring acute PLD activation in response to a stimulus, by using PMA as a model pharmacological agent to mimic activation of several signal transduction pathways. In the absence of a stimulus, however, it is known that PLD enzymes display a much lower but appreciable level of basal activity. The ability to detect this much lower level of basal PLD activity could permit the study of the consequences of aberrant PLD levels that occur in disease, notably in several cancers. Thus, further experiments set out to determine whether the azidoalcohol reporters displayed sufficient sensitivity to detect basal, endogenous PLD activity.

To accomplish this, HeLa cells were treated with 1 mM AzProp, followed by lipid extraction, SPAAC labeling with (1), and HPLC analysis. While short incubations of AzProp (e.g., 20 minutes) did not result in appreciable labeling, slightly longer labeling times of 2 hours led to detection of fluorescent phosphatidyl alcohols. Treatment with FIPI prevented phosphatidyl alcohol production, and use of the isoform-selective inhibitors VU0359595 and VU0364739 revealed that roughly half of the unstimulated PLD activity in HeLa cells can be attributed to each of PLD1 and PLD2.

To image sites of basal PLD activity within live cells, cells were treated with 1 mM AzProp for 2 hours and rinsed. The SPAAC reaction was then performed using (1). Analysis of populations of labeled cells by flow cytometry revealed a modest amount of fluorescence that was four-fold higher in cells treated with AzProp than in cells treated with no alcohol. Importantly, the use of FIPI and the isoform-selective inhibitors in these flow cytometry experiments gave results that were consistent with the in vitro lipid analysis, which indicates that the AzProp-dependent cellular fluorescence was due entirely to PLD enzymes and split evenly between the activities of PLD1 and PLD2.

Further experiments then examined the distribution of basal PLD activity at both the cellular and subcellular levels. At the cellular level, a striking heterogeneity was observed, wherein a small subset of cells exhibited high fluorescence, while the majority of cells exhibited much lower fluorescence. When similar labeling of basal PLD activity was performed in the presence of the PLD1 isoform-selective inhibitor VU0359595, the disappearance of high-fluorescence cells by confocal microscopy was observed, while treatment with the PLD2 inhibitor VU0364739 did not eliminate the high-fluorescence population. Thus, at the cellular level, the high fluorescence of a minority of cells can be attributed to PLD1 activity, and the moderate fluorescence in the majority of cells to PLD2. These data are consistent with the constitutive but modest activity of PLD2 compared to the highly inducible activity of PLD1. However, the heterogeneity of PLD1 at the cellular level is unexpected and quite different from the case where PLD1 activity is stimulated by PMA, where virtually all of cells exhibited high and roughly equivalent levels of fluorescence.

The subcellular localization of AzProp-marked basal PLD activity appeared to be similar to that of AzProp-marked, PMA-stimulated PLD enzymes, that is localized to a mixture of ER, Golgi, endosomal, and lysosomal membranes. Isoform-selective inhibitors were used to probe the relative contributions of each PLD isoform to PA biosynthetic activity on different organelle membranes. Use of the PLD1-selective inhibitor VU0359595 led to selective disappearance of most of the ER-derived fluorescence but only a portion of the Golgi-derived fluorescence. By contrast, the PLD2-selective inhibitor VU0364739 caused a decrease in Golgi-derived fluorescence but had minimal effect on ER-derived fluorescence. Thus, it can be concluded that, in HeLa cells, the bulk of ER-localized, basal PLD activity is due to PLD1, whereas PLD activity on Golgi membranes is due to a roughly equal mix of PLD1 and PLD2.

Figure 4:
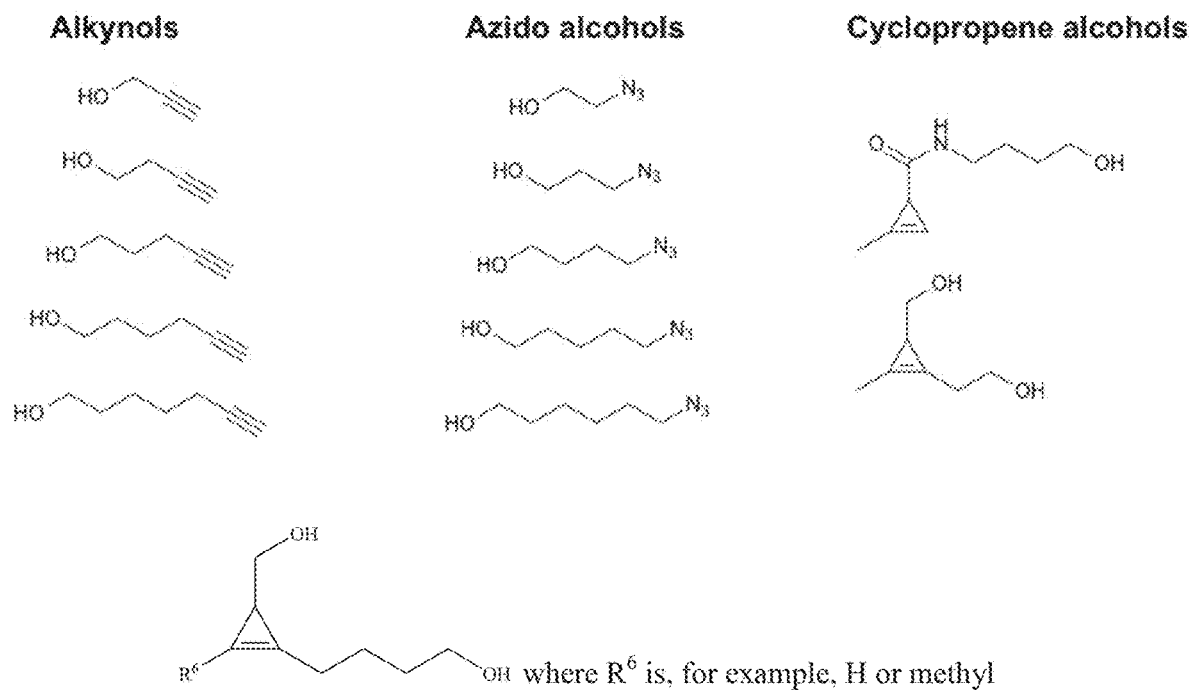
FIG. 4 shows exemplary alkynols, azido alcohols, and cyclopropene alcohols as possible exogenous functionalized alcohols that can undergo transphosphatidylation with PC in the presence of PLD to produce functionalized phosphatidyl alcohols that can be subsequently attached to a detectable label by appropriate crosslinking chemistry (e.g., azide-alkyne cycloaddition process).
Figure 5:
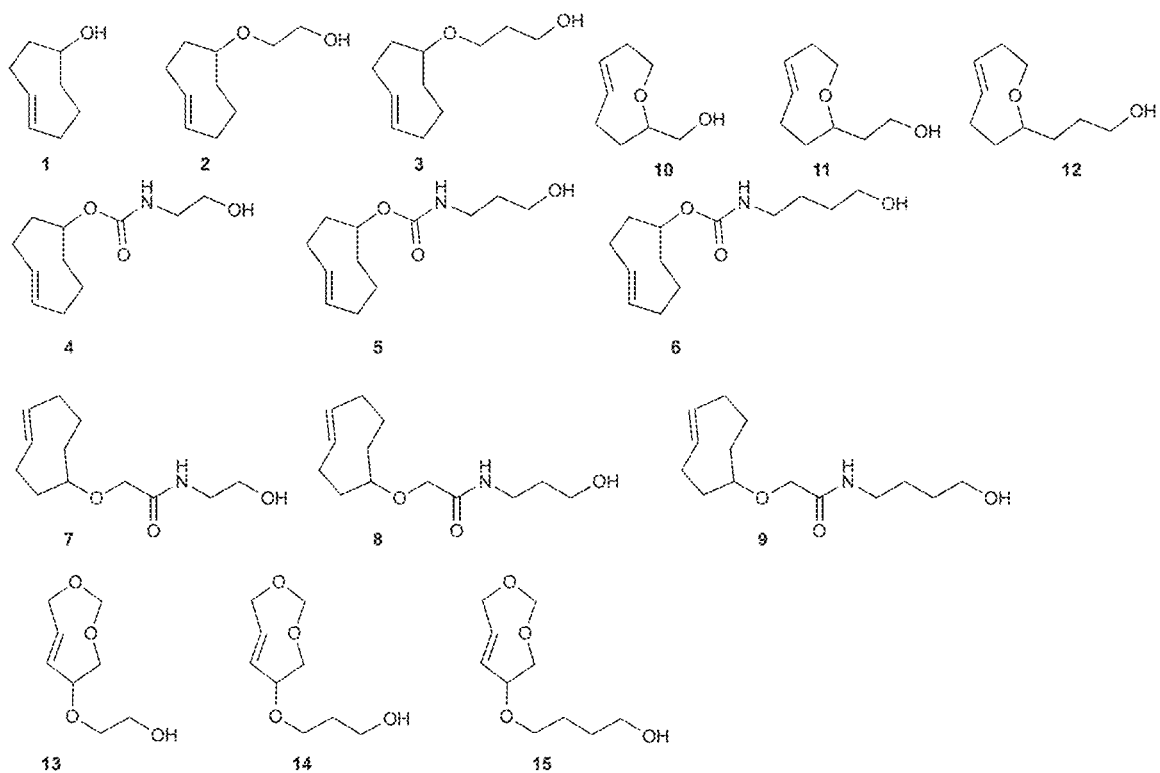
FIG. 5 shows exemplary trans-cyclooctene alcohols as possible exogenous functionalized alcohols that can undergo transphosphatidylation with PC in the presence of PLD to produce functionalized phosphatidyl alcohols that can be subsequently attached to a detectable label by appropriate crosslinking chemistry (e.g., IEDDA process).

It has also been shown that, in addition to the primary alkynols and azido alcohols, some cyclopropene and trans-cyclooctene alcohols are substrates of human and *Streptomyces* PLD enzymes. These strained alkene groups can participate in inverse electron-demand Diels-Alder (IEDDA) cycloadditions with tetrazine reagents to append fluorophores with very rapid kinetics. It has also herein been found that a secondary azidoalcohol is a weak PLD substrate. FIG. 4 shows exemplary alkynols, azido alcohols, and cyclopropene alcohols as possible exogenous functionalized alcohols that can undergo transphosphatidylation with PC in the presence of PLD to produce functionalized phosphatidyl alcohols that can be subsequently attached to a detectable label by appropriate crosslinking chemistry (e.g., azide-alkyne cycloaddition process). FIG. 5 shows exemplary trans-cyclooctene alcohols as possible exogenous functionalized alcohols that can undergo transphosphatidylation with PC in the presence of PLD to produce functionalized phosphatidyl alcohols that can be subsequently attached to a detectable label by appropriate crosslinking chemistry (e.g., IEDDA process).

Figure 6:
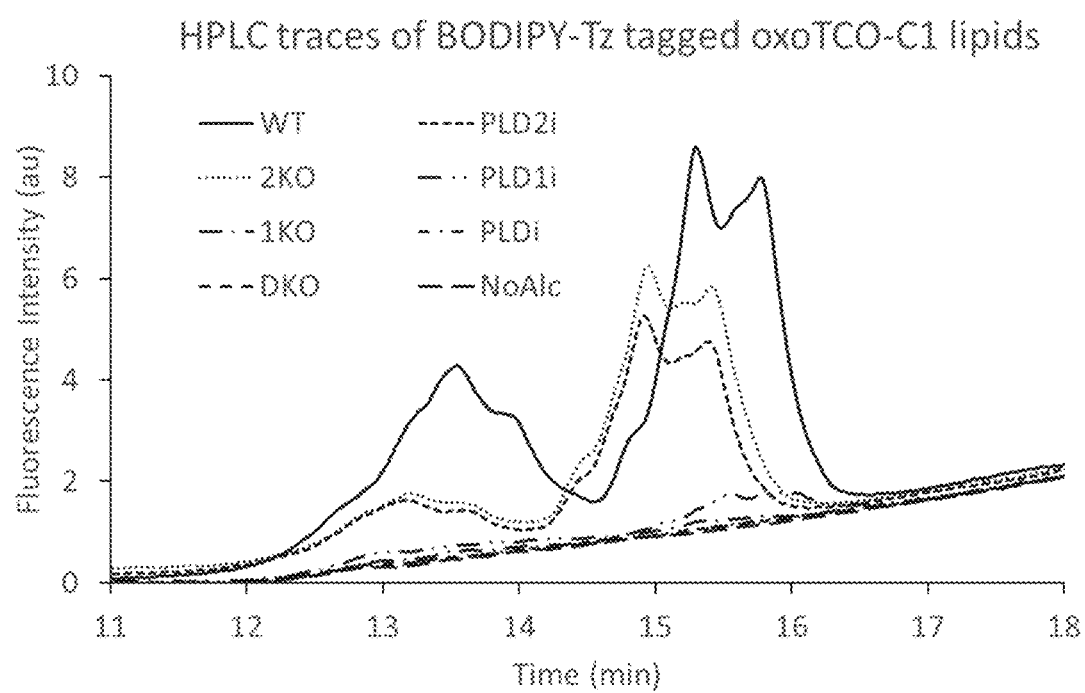
FIG. 6 is a graph showing HPLC traces of BODIPY-Tz (Tz=tetrazine) tagged oxo-transcyclooctene with one-carbon linker (oxoTCO-C1) lipids as obtained by fluorescence-coupled normal phase HPLC. PLDi, PLD1i, and PLD2i indicate the use of pan (PLDi) and isoform-selective (PLD1i and PLD2i) inhibitors for the enzymes during the oxoTCO+PMA step, and 1KO, 2KO, and DKO indicate the use of isogenic CRISPRCas9-generated PLD1 and PLD2 single knockout (1KO, 2KO) or double knockout (DKO) cell lines.

FIG. 6 is a graph showing HPLC traces of BODIPY-Tz tagged oxo-transcyclooocene lipids as obtained by fluorescence-coupled normal phase HPLC. Validation that oxo-transcyclooctene alcohol (oxoTCO-C1, compound 5, r=1) is accepted by endogenous mammalian phospholipase D enzymes. HeLa cells were treated with the compound and phorbol-12-myristate-13-acetate (PMA) to stimulate endogenous PLDs. Lipid extracts were generated by the Bligh-Dyer method and tagged with a BODIPY-tetrazine reagent by IEDDA, followed by analysis via fluorescence-coupled normal-phase HPLC. PLDi, PLD1i, and PLD2i indicate the use of pan (PLDi) and isoform-selective (PLD1i and PLD2i) inhibitors for the enzymes during the oxoTCO+PMA step, and 1KO, 2KO, and DKO indicate the use of isogenic CRISPRCas9-generated PLD1 and PLD2 single knockout (1 KO, 2KO) or double knockout (DKO) cell lines. WT refers to wild-type cells, and NoAlc refers to the omission of oxoTCO in wild-type cells.

Table 1 below is a list of identified functionalized phosphatidyl alcohols isolated from cells treated with oxo-transcyclooctenyl alcohol (compound 5, r=1). Lipid extracts were reacted with a tetrazine-amine via IEDDA and detected by LC-TOF-MS. Indicated are calculated and expected masses of functionalized phosphatidyl alcohol products, listed as total number of carbons:number of double bonds.

TABLE 1

| Functionalized phosphatidyl alcohol (tail composition) | calcd | found |
|---|---|---|
| 36:1 | 1000.711 | 1000.702 |
| 36:2 | 998.6957 | 998.6956 |
| 36:3 | 996.68 | 996.6712 |
| 36:4 | 994.6643 | 994.6646 |
| 36:5 | 992.6486 | 992.6522 |
| 34:0 | 974.6958 | 974.6888 |
| 34:1 | 972.6801 | 972.6791 |
| 34:2 | 970.6644 | 970.6671 |
| 32:0 | 946.6645 | 946.6674 |
| 32:1 | 944.6488 | 944.6512 |
| 32:2 | 942.6331 | 942.6388 |
| 30:0 | 918.6332 | 918.635 |
| 30:1 | 916.6175 | 916.623 |

Figure 7:
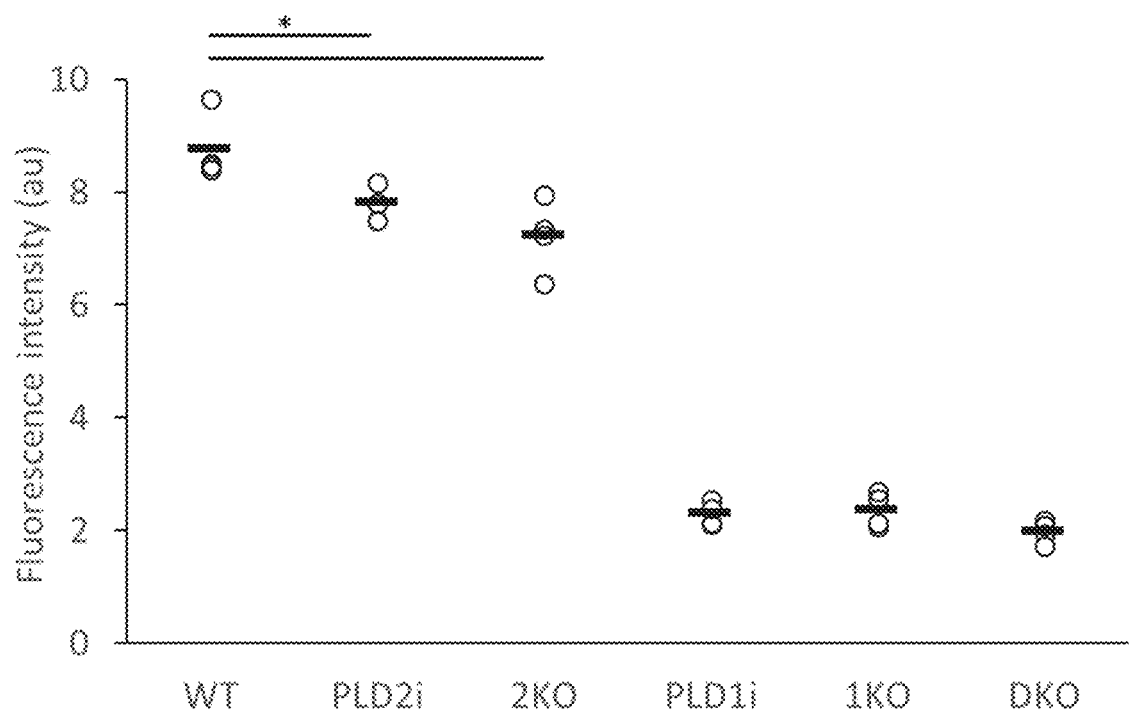
FIG. 7 is a fluorescence intensity plot of data providing further validation that oxo-transcyclooctene alcohol (oxoTCO-C1, compound 5, r=1) is accepted by endogenous mammalian phospholipase D enzymes and can be visualized within live cells. HeLa cells were treated with compound 5 and phorbol-12-myristate-13-acetate (PMA) to stimulate endogenous PLDs, rinsed, reacted with a BODIPY-tetrazine reagent by IEDDA, and analyzed by flow cytometry for fluorescence intensities. PLDi, PLD1i, and PLD2i indicate the use of pan (PLDi) and isoform-selective (PLD1i and PLD2i) inhibitors for the enzymes during the oxoTCO+PMA step, and 1KO, 2KO, and DKO indicate the use of isogenic CRISPRCas9-generated PLD1 and PLD2 single knockout (1KO, 2KO) or double knockout (DKO) cell lines. Graphs show mean fluorescence intensity of the population, and * indicates statistical significance of $p<0.05$.

FIG. 7 is a plot of data providing further validation that oxo-transcyclooctene alcohol (oxoTCO-C1, compound 5, r=1) is accepted by endogenous mammalian phospholipase D enzymes and can be visualized within live cells. HeLa cells were treated with compound 5 and phorbol-12-myristate-13-acetate (PMA) to stimulate endogenous PLDs, rinsed, reacted with a BODIPY-tetrazine reagent by IEDDA, and analyzed by flow cytometry for fluorescence intensities. PLDi, PLD1i, and PLD2i indicate the use of pan (PLDi) and isoform-selective (PLD1i and PLD2i) inhibitors for the enzymes during the oxoTCO+PMA step, and 1KO, 2KO, and DKO indicate the use of isogenic CRISPRCas9-generated PLD1 and PLD2 single knockout (1KO, 2KO) or double knockout (DKO) cell lines. Graphs show mean fluorescence intensity of the population, and * indicates statistical significance of $p<0.05$.

Figure 8:
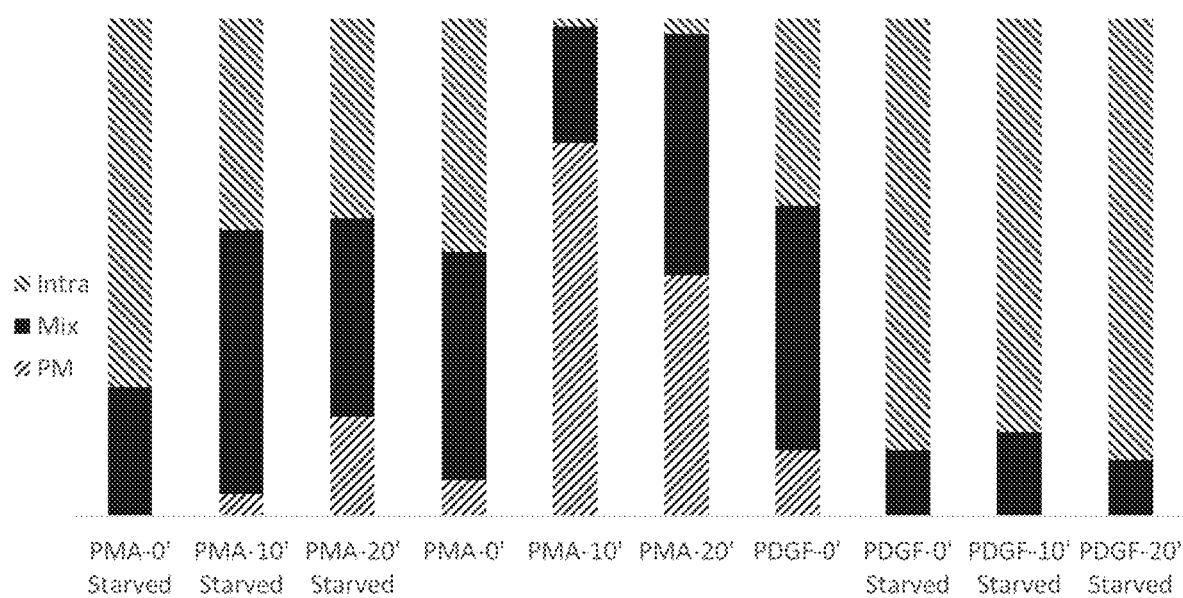
FIG. 8 is a bar chart showing quantification of live-cell imaging experiments demonstrating that oxo-transcyclooctene alcohol (oxoTCO-C1, compound 5, r=1) labeling can reveal dynamic changes in localization of PLD activity, wherein intra, mix, and PM refer to localization (intracellular, mixture of intra and PM, and plasma membrane, respectively), and different time delays after cellular stimulation with platelet-derived growth factor (PDGF) or phorbol-12-myristate-13-acetate (PMA), with or without prior serum starvation (starved).

FIG. 8 is a bar chart showing quantification of live-cell imaging experiments demonstrating that oxo-transcyclooctene alcohol (oxoTCO-C1, compound 5, r=1) labeling can reveal dynamic changes in localization of PLD activity. NIH 3T3 cells were, where indicated, serum-starved overnight, and then treated with the indicated stimulus (phorbol 12-myristate-13-acetate, PMA, or platelet-derived growth factor, PDGF) for specified durations, followed by incubation of the same stimulus and oxoTCO-C1 for 5 min at 37° C. The cells were then rinsed briefly with PBS and rinsed in media for 1 min at 37° C. The media was aspirated and 200 μL buffer was placed into the glass well at the center. The dish was then put on the microscope and snapshots taken every 3 s while a fluorogenic BODIPY-tetrazine in PBS was added into the well. Each cell in the third frame after fluorophore addition (i.e. the snapshots taken at t=9 s) was analyzed for subcellular localization of fluorescence signals as indicators of PLD activities and binned according to three categories: Intra=mostly intracellular; Mix=both plasma membrane and intracellular; PM=mostly plasma membrane. Each bar represents the average fractions of each category from at least 3 biological replicates.

While there have been shown and described what are at present considered the preferred embodiments of the invention, those skilled in the art may make various changes and modifications which remain within the scope of the invention defined by the appended claims.

What is claimed is:

1. A method for detecting phospholipase D (PLD) activity in a cell, the method comprising:

(i) providing a cell containing endogenous PLD;
(ii) contacting said cell with an exogenous alcohol of the formula HO—(CH$_2$)$_n$—Y, wherein Y is a first functional group and n is an integer of 1-12;
(iii) stimulating the endogenous PLD in said cell while said cell is in contact with said exogenous alcohol, whereby the stimulated PLD catalyzes a transphosphatidylation reaction in the cell between phosphatidylcholine or a derivative thereof and said exogenous alcohol to form a phosphatidyl alcohol reaction product containing said first functional group in unreacted form, wherein the transphosphatidylation reaction catalyzed by PLD in the cell in step (iii) proceeds according to the following reaction scheme:

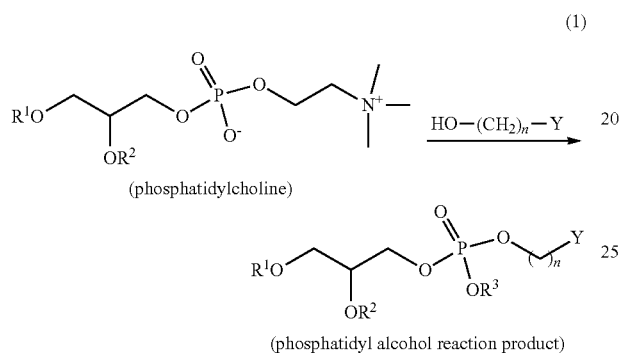

(phosphatidylcholine)

(phosphatidyl alcohol reaction product)

wherein R$^1$ and R$^2$ are independently selected from acyl fatty acid groups —C(O)R, wherein R is independently selected from alkyl or alkenyl groups having at least 12 carbon atoms; and R$^3$ is a H atom, hydrocarbon group having 1-3 carbon atoms, or a cationic species;
(iv) reacting said phosphatidyl alcohol reaction product with a detectable label of the formula D-Y' wherein D is a detectable group and Y' is a second functional group reactive with the first functional group Y on said phosphatidyl alcohol reaction product, to form a labeled phosphatidyl alcohol reaction product containing said detectable label, wherein step (iv) proceeds according to the following reaction scheme:

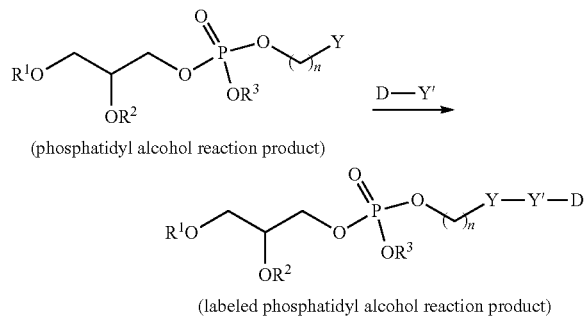

(phosphatidyl alcohol reaction product)

(labeled phosphatidyl alcohol reaction product)

wherein Y—Y' represents the linkage formed by reaction between Y and Y'; and
(v) detecting said labeled phosphatidyl alcohol reaction product.

2. The method of claim 1, wherein detecting comprises imaging.

3. The method of claim 1, wherein said detectable label is a fluorophore, radioisotope, or metal-containing nanoparticle.

4. The method of claim 1, wherein said exogenous alcohol is selected from the group consisting of alkynols, azido alcohols, cyclopropene alcohols, and trans-cyclooctene alcohols.

5. The method of claim 1, wherein said exogenous alcohol is selected from the group consisting of alkynols and azido alcohols.

6. The method of claim 1, wherein said exogenous alcohol is an alkynol, and said alkynol reacts with said phosphatidylcholine or a derivative thereof to form said phosphatidyl alcohol reaction product, which contains an alkyne functional group in available form, as provided by the alkynol.

7. The method of claim 6, wherein said phosphatidyl alcohol reaction product has the following structure:

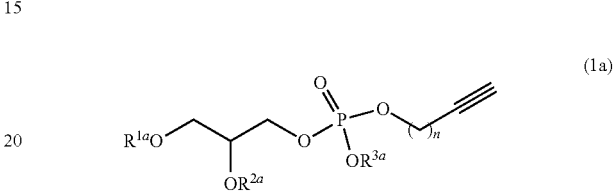

wherein:
R$^{1a}$ and R$^{a2}$ are independently selected from acyl fatty acid groups —C(O)R, wherein R is independently selected from alkyl or alkenyl groups having at least 12 carbon atoms;
R$^{3a}$ is a H atom, hydrocarbon group having 1-3 carbon atoms, or a cationic species; and
n is an integer of 1-12.

8. The method of claim 6, wherein said alkynol contains 3-14 carbon atoms.

9. The method of claim 6, wherein said alkynol contains the alkyne group and hydroxy group separated by the greatest number of carbon atoms in said alkynol.

10. The method of claim 6, wherein said alkynol is selected from the group consisting of propargyl alcohol, 3-butyn-1-ol, 4-pentyn-1-ol, 5-hexyn-1-ol, 6-heptyn-1-ol, 7-octyn-1ol, 8-nonyn-1-ol, 9-decyn-1-ol, 10-undecyn-1-ol, and 11-dodecyn-1-ol.

11. The method of claim 6, wherein the detectable label is a fluorophore, and the resulting labeled phosphatidyl alcohol reaction product is a fluorophore-labeled phosphatidyl alcohol reaction product.

12. The method of claim 11, wherein said fluorophore is an azide-functionalized fluorophore, and said phosphatidyl alcohol reaction product is reacted, via its alkyne group, with said azide-functionalized fluorophore, via its azide group, under conditions where said alkyne group and azide group undergo an azide-alkyne cycloaddition reaction so as to form said fluorophore-labeled phosphatidyl alcohol reaction product.

13. The method of claim 12, wherein said azide-alkyne cycloaddition reaction is copper-catalyzed.

14. The method of claim 12, wherein said azide-alkyne cycloaddition reaction is a copper-free strain-promoted azide-alkyne cycloaddition, wherein said alkyne group is within a cycloalkyne ring.

15. The method of claim 1, wherein said exogenous alcohol is an azido alcohol, and said azido alcohol reacts with said phosphatidylcholine or a derivative thereof to form said phosphatidyl alcohol reaction product, which contains an azido functional group in available form, as provided by the azido alcohol.

16. The method of claim 15, wherein said phosphatidyl alcohol reaction product has the following structure:

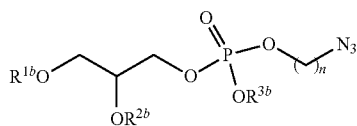

(1b)

wherein:
$R^{1b}$ and $R^{2b}$ are independently selected from acyl fatty acid groups —C(O)R, wherein R is independently selected from alkyl or alkenyl groups having at least 12 carbon atoms;
$R^{3b}$ is a H atom, hydrocarbon group having 1-3 carbon atoms, or a cationic species; and
n is an integer of 1-12.

17. The method of claim 15, wherein said azido alcohol contains 2-12 carbon atoms.

18. The method of claim 15, wherein said azido alcohol contains the azide group and hydroxy group separated by the greatest number of carbon atoms in said alkynol.

19. The method of claim 15, wherein said azido alcohol is selected from the group consisting of 2-azidoethanol, 3-azido-1-propanol, 4-azido-1-butanol, 5-azido-1-pentanol, 6-azido-1-hexanol, 7-azido-1-heptanol, 8-azido-1-octanol, 9-azido-1-nonanol, 10-azido-1-decanol, 11-azido-1-undecanol, and 12-azido-1-dodecanol.

20. The method of claim 15, wherein the detectable label is a fluorophore, and the labeled phosphatidyl alcohol reaction product is a fluorophore-labeled phosphatidyl alcohol reaction product.

21. The method of claim 20, wherein said fluorophore is an alkyne-functionalized fluorophore, and said phosphatidyl alcohol reaction product is reacted, via its azido group, with said alkyne-functionalized fluorophore, via its alkyne group, under conditions where said alkyne group and azide group undergo an azide-alkyne cycloaddition reaction so as to form said fluorophore-labeled phosphatidyl alcohol reaction product.

22. The method of claim 21, wherein said azide-alkyne cycloaddition reaction is copper-catalyzed.

23. The method of claim 21, wherein said azide-alkyne cycloaddition reaction is a copper-free strain-promoted azide-alkyne cycloaddition, wherein said alkyne group is within a cycloalkyne ring.

24. The method of claim 1, wherein said exogenous alcohol is a cyclopropene alcohol or trans-cyclooctene alcohol, and said cyclopropene alcohol or trans-cyclooctene alcohol reacts with said phosphatidylcholine or a derivative thereof to form said phosphatidyl alcohol reaction product, which contains a cyclopropene or trans-cyclooctene functional group in available form, as provided by the cyclopropene alcohol or trans-cyclooctene alcohol.

25. The method of claim 24, wherein said phosphatidyl alcohol reaction product has the following structure:

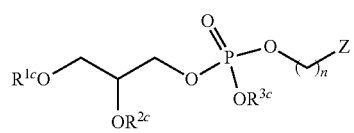

(1c)

wherein:
$R^{1c}$ and $R^{2c}$ are independently selected from acyl fatty acid groups —C(O)R, wherein R is independently selected from alkyl or alkenyl groups having at least 12 carbon atoms;

$R^{3c}$ is a H atom, hydrocarbon group having 1-3 carbon atoms, or a cationic species;
n is an integer of 1-12; and
Z is a cyclopropene or trans-cyclooctene functional group.

26. The method of claim 24, wherein the detectable label is a fluorophore, and the resulting labeled phosphatidyl alcohol reaction product is a fluorophore-labeled phosphatidyl alcohol reaction product.

27. The method of claim 26, wherein said fluorophore is a tetrazine-functionalized fluorophore, and said phosphatidyl alcohol reaction product is reacted, via its cyclopropene or trans-cyclooctene group, with said tetrazine-functionalized fluorophore, via its tetrazine group, under conditions where said cyclopropene or trans-cyclooctene group undergoes an inverse electron-demand Diels-Alder (IEDDA) cycloaddition reaction with said tetrazine so as to form said fluorophore-labeled phosphatidyl alcohol reaction product.

28. A method for detecting phospholipase D(PLD) activity in a cell, the method comprising:
(i) providing a cell containing endogenous PLD;
(ii) contacting said cell with an exogenous alcohol of the formula HO—$(CH_2)_n$—Y, wherein Y is a first functional group and n is an integer of 1-12;
(iii) stimulating the endogenous PLD in said cell by contacting the cell with phorbol 12-myristate-13-acetate (PMA) or platelet-derived growth factor (PDGF) while said cell is in contact with said exogenous alcohol, whereby the stimulated PLD catalyzes a transphosphatidylation reaction in the cell between phosphatidylcholine or a derivative thereof and said exogenous alcohol to form a phosphatidyl alcohol reaction product containing said first functional group in unreacted form, wherein the transphosphatidylation reaction catalyzed by PLD in the cell in step (iii) proceeds according to the following reaction scheme:

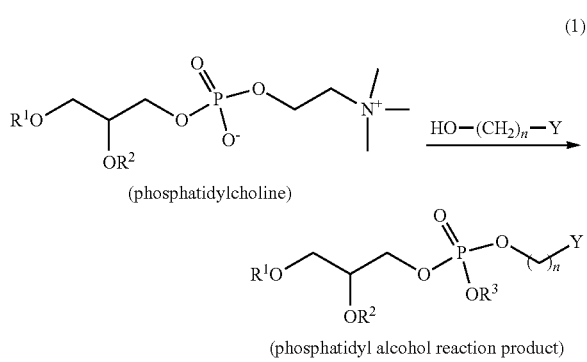

(1)

(phosphatidylcholine)

(phosphatidyl alcohol reaction product)

wherein $R^1$ and $R^2$ are independently selected from acyl fatty acid groups —C(O)R, wherein R is independently selected from alkyl or alkenyl groups having at least 12 carbon atoms; and $R^3$ is a H atom, hydrocarbon group having 1-3 carbon atoms, or a cationic species;

(iv) reacting said phosphatidyl alcohol reaction product with a detectable label of the formula D-Y' wherein D is a detectable group and Y' is a second functional group reactive with the first functional group Y on said phosphatidyl alcohol reaction product, to form a labeled phosphatidyl alcohol reaction product containing said detectable label, wherein step (iv) proceeds according to the following reaction scheme:

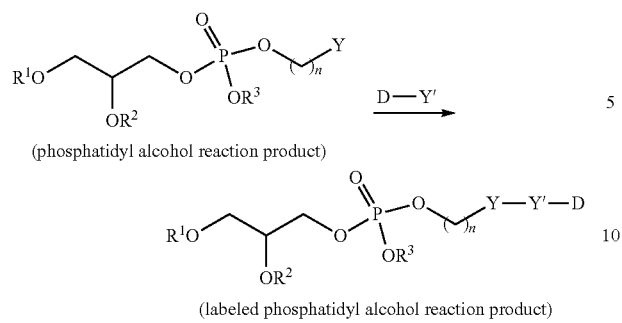
wherein Y—Y' represents the linkage formed by reaction between Y and Y'; and
(v) detecting said labeled phosphatidyl alcohol reaction product.
* * * * *